US011510955B2

(12) United States Patent
Shin et al.

(10) Patent No.: US 11,510,955 B2
(45) Date of Patent: Nov. 29, 2022

(54) **COMPOSITION COMPRISING A COMBINED HERB EXTRACT OF *SALVIA PLEBIA* AND RED GINSENG AS ACTIVE INGREDIENTS FOR PREVENTING OR TREATING A RESPIRATORY INFLAMMATION AND THE USE THEREOF**

(71) Applicants: KT & G CORPORATION, Daejeon (KR); KOREA GINSENG CORP., Daejeon (KR)

(72) Inventors: Han-Jae Shin, Daejeon (KR); Hyo Keun Kim, Daejeon (KR); Moon-Yong Lee, Daejeon (KR); Hyo-Min Gwak, Daejeon (KR); Hye-Jeong Min, Daejeon (KR); Young-Sin Kim, Daejeon (KR); Chang Kyun Han, Daejeon (KR); Jongsu Kyung, Daejeon (KR); Gyo In, Daejeon (KR); Jong Han Kim, Daejeon (KR); Sung Won Kim, Daejeon (KR); Kyoung Hwa Jang, Daejeon (KR); Seung-Hyung Kim, Daejeon (KR)

(73) Assignees: KT&G CORPORATION, Daejeon (KR); KOREA GINSENG CORP., Daejeon (KR)

( * ) Notice: Subject to any disclaimer, the term of this patent is extended or adjusted under 35 U.S.C. 154(b) by 0 days.

(21) Appl. No.: 16/611,836

(22) PCT Filed: May 10, 2018

(86) PCT No.: PCT/KR2018/005361
§ 371 (c)(1),
(2) Date: Nov. 7, 2019

(87) PCT Pub. No.: WO2018/208094
PCT Pub. Date: Nov. 15, 2018

(65) Prior Publication Data
US 2020/0164016 A1    May 28, 2020

(30) Foreign Application Priority Data

May 11, 2017   (KR) .................. 10-2017-0058865

(51) Int. Cl.
*A61K 36/537*  (2006.01)
*A61P 11/06*  (2006.01)
(Continued)

(52) U.S. Cl.
CPC .......... *A61K 36/537* (2013.01); *A61K 9/0095* (2013.01); *A61K 9/10* (2013.01);
(Continued)

(58) Field of Classification Search
None
See application file for complete search history.

(56) References Cited

U.S. PATENT DOCUMENTS

2011/0086052 A1   4/2011   Adamko et al.
2015/0174186 A1   6/2015   Rho et al.

FOREIGN PATENT DOCUMENTS

CN   1438013 A   8/2003
CN   102014941 A   4/2011
(Continued)

OTHER PUBLICATIONS

Tashkin et al. (Bronchodilator responsiveness in patients with COPD, European Respiratory Journal 2008 31: 742-750) (Year: 2008).*
(Continued)

*Primary Examiner* — Melissa S Mercier
(74) *Attorney, Agent, or Firm* — Sughrue Mion, PLLC

(57) ABSTRACT

The present invention relates to a composition and health functional food for preventing and treating a respiratory inflammation disease using a mixed herbal mixture. Through various experiments, for example, determination of
(Continued)

the cell number of BAL (bronchoalveolar lavage) (Experimental Example 1); Determination of CD11b+/Gr-1+ ratio in leukocyte within BAL fluid (Experimental Example 2); Determination of expressed RNA level of inflammatory cytokines in lung tissue (Experimental Example 3); Determination of expressed RNA level of inflammatory cytokines in BALF (Experimental Example 4); Lung histology (Experimental Example 5); Brief Clinical test (Experimental Example 7) etc, it has been verified that the inventive combined extract showed more potent inhibiting effect on respiratory inflammation disease than each herb extract. Therefore, the herbal extract of the present invention can be usefully used in a pharmaceutical composition, health functional food, and health supplement food for preventing and treating respiratory inflammation disease.

9 Claims, 1 Drawing Sheet

Specification includes a Sequence Listing.

(51) Int. Cl.
| | |
|---|---|
| A61P 11/08 | (2006.01) |
| A61K 9/00 | (2006.01) |
| A61K 9/10 | (2006.01) |
| A61K 9/16 | (2006.01) |
| A61K 9/20 | (2006.01) |
| A61K 9/48 | (2006.01) |
| A61K 36/258 | (2006.01) |

(52) U.S. Cl.
CPC .............. A61K 9/16 (2013.01); A61K 9/20 (2013.01); A61K 9/4858 (2013.01); A61K 36/258 (2013.01); A61P 11/06 (2018.01); A61P 11/08 (2018.01)

(56) References Cited

FOREIGN PATENT DOCUMENTS

| | | | |
|---|---|---|---|
| CN | 102657698 | A | 9/2012 |
| CN | 104349787 | A | 2/2015 |
| CN | 104644656 | A | 5/2015 |
| KR | 1999-015091 | A | 3/1999 |
| KR | 1020120129474 | * | 5/2011 |
| KR | 1020120129474 | A * | 5/2011 |
| KR | 1020120129474 | A | 11/2012 |
| KR | 1020160146007 | A * | 12/2012 |
| KR | 1020130129868 | A | 11/2013 |
| KR | 10-2015-0007037 | A | 1/2015 |
| KR | 1020150026579 | A | 3/2015 |
| KR | 1020160021038 | A | 2/2016 |
| KR | 10-2016-0127328 | A | 11/2016 |
| KR | 1020160146007 | A * | 12/2016 |
| KR | 1020160146007 | A * | 12/2016 |
| KR | 1020160176007 | * | 12/2016 |
| KR | 101770766 | B2 | 8/2017 |
| WO | 2016/001922 | A1 | 1/2016 |
| WO | 2018208094 | A2 | 11/2018 |

OTHER PUBLICATIONS

Burney et al. (Forced vital capacity, airway obstruction and survival in a general sample from the USA, Thorax 2011; 66: 49-54) (Year: 2011).*

Aaron et al. (Time course and pattern of COPD exacerbation onset, Thorax, 2012:67:238-243). (Year: 2012).*
Minoguchi K and Adachi M., Pathophysiology of asthma. In: Cherniack NS, Altose MD, Homma I. editors. Rehabilitation of the patient with respiratory disease. New York: McGraw-Hill, 1999, pp. 97-104.
Elias JA et al., J Clin Invest., 111, pp. 291-297, 2003.
Maggi E., Immunotechnology 3, pp. 233-244, 1998.
Pawankar R. Curr. Opin. Allergy Clin. Immunol., 1, pp. 3-6, 2001.
Barnes PJ et al., Phamacol. Rev. 50, pp. 515-596, 1998.
Dong Soon Kim, Young Sam Kim, Ki-Suck Jung, Jung Hyun Chang, Chae-Man Lim, Jae Ho Lee, Soo-Taek Uh, Jae Jeong Shim, and Woo Jin Lew, on behalf of the Korean Academy of Tuberculosis and Respiratory Diseases, Am J Respir Crit Care Med vol. 172. pp. 842-847, 2005.
Don D. Sin and S. F. Paul Man, Chronic Obstructive Pulmonary Disease as a Risk Factor for Cardiovascular Morbidity and Mortality, Proc Am Thorac Soc vol. 2. pp. 8-11, 2005.
A Sonia Buist, Mary Ann McBurnie, William M Vollmer, Suzanne Gillespie, Peter Burney, David M Mannino, Ana M B Menezes, Sean D Sullivan, Todd A Lee, Kevin B Weiss, Robert L Jensen, Guy B Marks, Amund Gulsvik, Ewa Nizankowska-Mogilnicka, International variation in the prevalence of COPD (The BOLD Study): a population-based prevalence study, Lancet, vol. 370;741-750, Sep. 1, 2007.
Barnes PJ (2000b) Mechanisms in COPD: differences from asthma. Chest 117(Suppl): 10S-14S.
Saetta M, Turato G, Maestrelli P, Mapp CE, and Fabbri LM (2001) Cellular and structural bases of chronic obstructive pulmonary disease. (Am. J. Respir. Crit. Care Med. 163:1304-1309.
Bae E. A. et al. 2006, Inhibitory effect of Korean red ginseng and its genuine constituents ginsenosides Rg3, Rf and Rh2 in mouse passive cutaneous anaphylaxis reaction and contact dermatitis models, Biol. Pharm, Bull, 29; pp. 1862-1867.
Schins et al., Toxicol. Appl. Pharmacol., 195(1), pp. 1-11, 2004.
Smith et al., Toxicol. Sci., 93(2), pp. 390-399, 2006.
Beutner E. H., bacteriological Reviews, 25(1), pp. 49-76, 1961.
Brandt E.B. et al., J. Allergy Clin. Immunol., 132(5), pp. 1194-1204, 2013.
Nandedkar SD. et al., Blood, 112(6), pp. 2529-2538, 2008.
Biological Research, 2016, vol. 49, Article No. 41, internal pp. 1-11.
Journal of Ginseng Research, 2015, vol. 39, No. 1, pp. 38-45.
Journal of Ginseng Research, 2013, vol. 37. No. 2, pp. 167-175.
International Search Report, PCT/KR2018/005361, dated Nov. 14, 2018.
International Application Status Report, PCT/KR2018/005361, dated Sep. 23, 2019.
Communication dated Mar. 22, 2022 from the Japanese Patent Office in JP Application No. 2019-562656.
Communication dated Jun. 28, 2021 from The State Intellectual Property Office of P.R. of China in Application No. 201880029176.6.
Liu Hong-Fang et al., "Color Atlas of Common Chinese Herbal Medicines", Liaoning Science and Technology Publishing House, Jan. 31, 2017, 1st Edition, pp. 107 and 395 (3 pages total).
Jin Guangri et al., "The inhibitory effects of water extracts of Red Ginseng on airway inflamation in mouse with bronchial asthma", China Academic Journal Electronic Publishing House, 2015, vol. 31, No. 4, pp. 129-132 (4 pages total).
J.L. Shergis et al., "Therapeutic potential of Panax ginseng and ginsenosides in the treatment of chronic obstructive pulmonary disease", Complementary Therapies in Medicine, 2014, vol. 22, No. 4, pp. 944-953 (10 pages total).
Office Action dated Jun. 16, 2022 issued by the Chinese Patent Office in Chinese Application No. 202111448135.0.

* cited by examiner

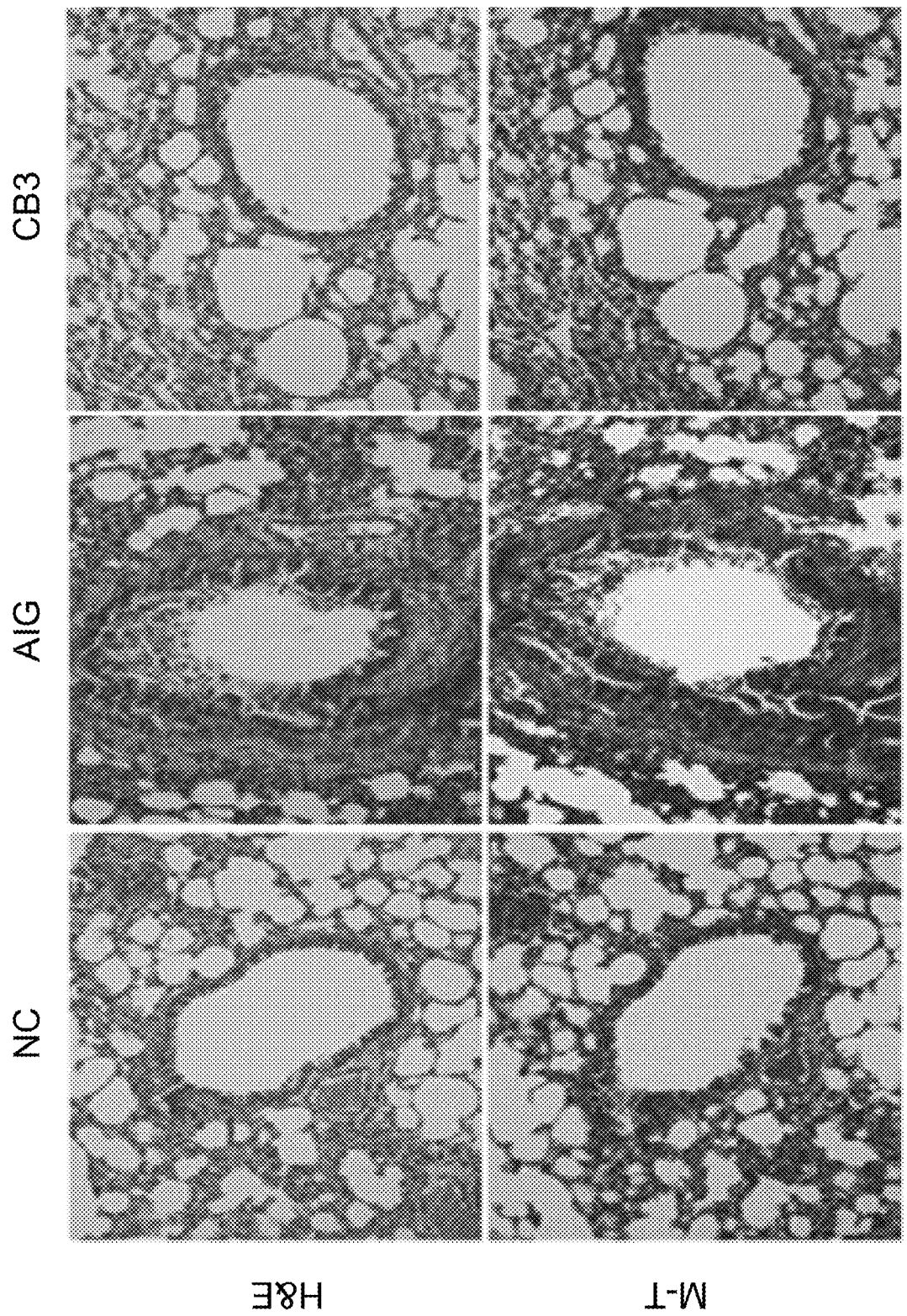

SEQUENCE LISTING

<160> NUMBER OF SEQ ID NOS: 5

<210> SEQ ID NO 1
<211> LENGTH: 24
<212> TYPE: DNA
<213> ORGANISM: Unknown
<220> FEATURE:
<223> OTHER INFORMATION: Murine

<400> SEQUENCE: 1

```
agaatatctt tcaggacccc tgct                                          24

<210> SEQ ID NO 2
<211> LENGTH: 23
<212> TYPE: DNA
<213> ORGANISM: Unknown
<220> FEATURE:
<223> OTHER INFORMATION: Murine

<400> SEQUENCE: 2
acaccagtgc tgagcatact ttt                                           23

<210> SEQ ID NO 3
<211> LENGTH: 20
<212> TYPE: DNA
<213> ORGANISM: Unknown
<220> FEATURE:
<223> OTHER INFORMATION: Murine

<400> SEQUENCE: 3
attctccaca ccctgtttcg                                               20

<210> SEQ ID NO 4
<211> LENGTH: 20
<212> TYPE: DNA
<213> ORGANISM: Unknown
<220> FEATURE:
<223> OTHER INFORMATION: Murine

<400> SEQUENCE: 4
aaggtggtca ggaggaggac                                               20

<210> SEQ ID NO 5
<211> LENGTH: 26
<212> TYPE: DNA
<213> ORGANISM: Unknown
<220> FEATURE:
<223> OTHER INFORMATION: Murine

<400> SEQUENCE: 5
catgttccag tatgactcca ctcacg                                        26
```

COMPOSITION COMPRISING A COMBINED HERB EXTRACT OF *SALVIA PLEBIA* AND RED GINSENG AS ACTIVE INGREDIENTS FOR PREVENTING OR TREATING A RESPIRATORY INFLAMMATION AND THE USE THEREOF

TECHNICAL FIELD

The present invention is related to a composition comprising the combined herb extract of *Salvia plebeia* R. Br. and red ginseng as active ingredient for treating and preventing a respiratory inflammation and the use thereof.

BACKGROUND ART

Generally, an inflammatory response is a normal response of human body associated with an edema, a pain etc in case that a tissue or a cell received any invasion causing some organic change in the tissue or cell. Recently, various kinds of cytokines have been found to be involved in the inflammatory disease.

Allergic reaction may be classified into four categories, i.e., type I, II, III and IV according to the types of response or two categories, i.e., immediate type allergic reaction such as type I, II or III, and delayed type allergic reaction such as type IV according to the types of the period from the re-sensitization time caused by allergen to the onset time of reaction.

Among them, type I allergy, being involved in IgE antibody and called as anaphylaxis type allergy, causes to a bronchial asthma, atopic diseases such as dermatitis or gastroenteritis etc, allergic rhinitis such as pollenosis, allergic conjunctivitis, food allergy and the like.

Asthma is regarded as a complex syndrome of the airways that is characterized by various clinical symptoms, for example, cough, dyspnea caused by airflow obstruction, acute or chronic airway inflammation, airway hyperresponsiveness (AHR) and structural remodeling and can be reversibly or irreversibly recoverable. Most of asthma is allergic disease and is characterized by chronic airway inflammation and bronchial hyperresponsiveness (Minoguchi K and Adachi M., Pathophysiology of asthma. In: Cherniack N S, Altose M D, Homma I. editors. *Rehabilitation of the patient with respiratory disease*. New York: McGraw-Hill, 1999, pp 97-104).

The asthma can be classified two types, i.e., extrinsic asthma and intrinsic asthma. The extrinsic asthma is caused by exposing antigen and it is shown positive reaction in skin test or bronchial provocation test against the antigen. Usually causing ages is getting younger. It is mainly caused by House Dust Mite Dermatophagoides and pollen, epithelium of animal, fungi and so on. The intrinsic asthma is caused by upper respiratory infections, exercise, emotional instability, changing of climate of humidity and it is common to adult patient. Also, the IgE antigen of extrinsic asthma can be detected by skin test due to increasing IgE in serum.

With regards to pathophysiology, asthma is recognized by T-helper2 (Th2)-cell-driven chronic inflammation, and a variety of inflammatory mediators, such as cytokines, chemokines, signaling molecules, adhesion molecules and growth factors, from immune cells and structural cells in the airways are involved in various stages of asthma (Elias J A et al., *J Clin Invest.*, 111, pp 291-7, 2003). The activated inflammatory cells such as eosinophil, mast cells, alveolar macrophage etc in the bronchus of patients suffering from asthma, release various inflammatory mediators such as cystein leukotrienes, prostaglandins etc and is involved in potent bronchial constriction (Maggi E., Immunotechnology 3, pp 233-244, 1998; Pawankar R. Curr. Opin. Allergy Clin. Immunol., 1, pp 3-6, 2001; Barnes P J et al., Phamacol. Rev. 50, pp 515-596, 1998).

Accordingly, since the reproduction of various cytokines involved in inflammatory cell activation, such as IL-4, IL-5, IL-13 etc and IgE and reproduction of cystein leukotrienes released from the inflammatory cells are the main causes of inflammation, allergic reaction and asthma, there have been much studied to develop the inhibiting agents from the reproduction of those till now.

COPD (Chronic Obstructive Pulmonary Disease) has been reported as one of risk factor for cardiovascular morbidity and mortality and the fifth leading cause of death worldwide in 2001. The prevalence of chronic obstructive pulmonary disease based on Global Initiative for Chronic Obstructive Lung Disease (COLD) criteria (a ratio of FEV1 to FVC of less than 0.7) was 17.2% (men, 25.8%; women, 9.6%) among Koreans older than 45 years (Dong Soon Kim, Young Sam Kim, Ki-Suck Jung, Jung Hyun Chang, Chae-Man Lim, Jae Ho Lee, Soo-Taek Uh, Jae Jeong Shim, and Woo Jin Lew, on behalf of the Korean Academy of Tuberculosis and Respiratory Diseases, Am J Respir Crit Care Med Vol 172. pp 842-847, 2005; Don D. Sin and S. F. Paul Man, Chronic Obstructive Pulmonary Disease as a Risk Factor for Cardiovascular Morbidity and Mortality, Proc Am Thorac Soc Vol 2. pp 8-11, 2005; A Sonia Buist, Mary Ann McBurnie, William M Vollmer, Suzanne Gillespie, Peter Burney, David M Mannino, Ana M B Menezes, Sean D Sullivan, Todd A Lee, Kevin B Weiss, Robert L Jensen, Guy B Marks, Amund Gulsvik, Ewa Nizankowska-Mogilnicka, International variation in the prevalence of COPD (The BOLD Study): a population-based prevalence study, Lancet, Vol 370; 741-750, Sep. 1, 2007)

Most patients with COPD have all three pathological mechanisms (chronic obstructive bronchitis, emphysema, and mucus plugging) as all are induced by smoking, but they may differ in the proportion of emphysema and obstructive bronchitis. In developed countries, cigarette smoking is by far the most common cause of COPD, but there are several other risk factors, including air pollution (particularly, indoor air pollution from burning fuels), poor diet, and occupational exposure. COPD is characterized by acceleration in the normal decline of lung function seen with age. The slowly progressive airflow limitation leads to disability and premature death and is quite different from the variable airway obstruction and symptoms in asthma, which rarely progresses in severity.

There have been reported that the pathophysiological action and syndrome of COPD are fundamentally different from those of asthma. Although COPD and asthma both involve inflammation in the respiratory tract, there are marked differences in the nature of the inflammatory process, with differences in inflammatory cells, mediators, response to inflammation, anatomical distribution, and response to anti-inflammatory therapy, for example, (a) in respect to inflammatory cells, mast cell, eosinophils, D4+ cell (Th2), macrophages etc mainly act on the occurrence of asthma whereas neutrophils, CD8+(Tc) etc mainly act on the occurrence of COPD; (b) in respect to inflammatory mediators, leukotriens B, histamine, IL-4, IL-5, 11-13, eotaxin, RENTES, oxidative stress etc are mainly involved in the occurrence of asthma whereas TNF-alpha, IL-8, GRO-alpha etc are mainly involved in the occurrence of COPD; (c) in respect to inflammatory syndrome, asthma shows different inflammatory syndrome by acting on the overall pulmonary tract at early age, such as AHR (airway hyperresponsiveness), epithelial shedding, fibrosis, no parenchymal involvement, mucus secretion, relatively reversible airways obstruction, cough, sneezing, dyspnea etc from that of COPD, which occurs by acting on peripheral airways at adults and shows various phenomena such as, epithelial metaplasia, parenchymal destruction, relatively irreversible airways obstruction, chronic bronchitis, emphysema etc (Barnes P J (2000b) Mechanisms in COPD: differences from asthma. *Chest* 117 (Suppl): 10S-14S; Saetta M, Turato G, Maestrelli P, Mapp C E, and Fabbri L M (2001) Cellular and structural bases of chronic obstructive pulmonary disease. (*Am. J. Respir. Crit. Care Med.* 163: 1304-1309).

*Salvia plebeia* R. Br. belongs to Labiatae family and distributed at South Korea has been reported to comprise flavonoids, homoplantaginin, hispidulin, eupafolin, eupafolin-7-glucoside etc (B. S. Chung et al., YoungRim Press, $2^{nd}$ Edition, *DohaeHyangYakDaeSaJeon.*, pp 862-863, 1998).

There have been reported on the pharmacological composition comprising an extract or a purified fraction of *Salvia plebeia* R. Br. for preventing or treating STAT3-mediated disease (Korea patent publication No. 10-2013-0129868 A) and the composition comprising an extract of combined herbs of *Curcuma longa, Salvia plebeia, Elymus mollis, Chrysosplenium pilosum* var. *valdepilosum, Cyperus sanguinolentus, Chrysosplenium japonicum, Chrysosplenium trachyspernum*, and *Chrysosplenium flagelliferum* an active ingredient for preventing and treating allergic or non-allergic skin disease (Korea patent publication No. 10-2015-0026579 A).

A ginseng has been reported to be a representative nutritive tonic agent in Asian countries as well as other countries in the world and there are many genus of *Panax* genus plants belonged to Araliaceae, for example, *Panax ginseng* distributed or cultivated in far-eastern Asia region, *Panax quinquefolia* in America and Canada, *Panax notoginseng* in China, *Panax trifolia* in eastern region of north America, *Panax japonica* in Japan, China and Nepal, *Panax pseudoginseng* in Nepal, *Panax vietnamensis* in Vietnam, *Panax elegatior, Panax wangianus* and *Panax bipinratifidus*, etc.

The most important ingredient in the plant belonged to *Panax* genus is dammarane saponin having 1-4 numbers of saccharides and particularly, Korean ginseng comprises high amount of ginsenosides, such as ginsenoside Rb1, Rb2, Rc, Rd, Rg1, Re etc. Those saponins show various potency and pharmacological activities according to their structure.

There have been many attempts to process or modify *Panax* genus plants so as to increase their pharmacological potency, in particular, to modify the structure of ginsenoisides therein and the main component of *Panax* genus plant is a dammarane saponin such as ginsenosides $Rb_1$, $Rb_2$, Rc, Rd, $Rg_1$ and Re of which activities are different from each other in accordance with their chemical structures (Chung B. S. and Shin M. K.; HyangyakDaesacheon, Youngrimsa., pp 439-442, 1998).

In Korea, a ginseng is classified with several types according to the processed methods, i.e., an un-processed natural ginseng cultivated for more than 4 years called as a fresh ginseng, simple processed ginseng such as removing cortex of fresh ginseng called as a white ginseng, complex processed ginseng cultivated for more than 6 years old, i.e., the processing steps consisting of $1^{st}$ steaming with vapor at about 130° C. for 1 or 2 hours; cooling with the air; $2^{nd}$ steaming with vapor at about 70° C. for 7 to 10 hours; removing unnecessary parts such as beard root etc; and drying in drying room to make the water content of ginseng to the range from 12.5 to 13.5%, which is called as red ginseng, the most expensive and pharmacologically active form of ginseng.

There have been reported that red ginseng processed by the above-mentioned high-temperature treatment comprises various unique and modified ginsenosides which have not found in fresh ginseng or white ginseng, for example, ginsenosides $Rg_2$, $Rg_3$, $Rg_5$, $Rh_2$, $Rh_3$, $Rh_4$, $Rs_1$, $Rs_2$, $Rs_3$, etc. (Bae E. A. et al. 2006, Inhibitory effect of Korean red ginseng and its genuine constituents ginsenosides Rg3, Rf and Rh2 in mouse passive cutaneous anaphylaxis reaction and contact dermatitis models, Biol. Pharm, Bull, 29; pp 1862-1867).

The present inventors have developed the potent agents for treating respiratory inflammation disease from the various herbs, for example, the specific extract isolated from *Leonurus sibiricus* as an active ingredient for preventing or treating respiratory inflammatory disease (Korea patent registration No. 10-1770766 B2); specific extract or the compounds isolated from *Thuja orientalis* as an active ingredient for preventing or treating respiratory inflammatory disease (Korea patent publication No. KR 10-2016-0021038 A) etc.

However, there has been not reported or disclosed about the therapeutic effect of the extract of combined herbs consisting *Salvia plebeia* R. Br. and red ginseng as described above on a respiratory inflammation disease in any of above cited literatures, the disclosures of which are incorporated herein by reference.

DISCLOSURE

Technical Problem

Therefore, the present inventors have endeavored to find the effective herb formulation for treating and preventing a respiratory inflammation disease and the combined herb composition shows more potent treating effect on a respiratory inflammation than the individual herb composition, which is confirmed by various experiments, for example, determination of the cell number of BAL (bronchoalveolar lavage) (Experimental Example 1) to confirm synergistically potent inhibiting activity on the cell number in BAL (bronchoalveolar lavage); Determination of CD11b+/Gr-1+ ratio in leukocyte within BAL fluid (Experimental Example 2) to confirm synergistically potent inhibiting activity on the CD11b+/Gr-1+ ratio in leukocyte within BAL fluid; Determination of expressed RNA level of inflammatory cytokines in lung tissue (Experimental Example 3) to confirm the synergistically potent inhibiting activity on the expressed RNA level of inflammatory cytokines in lung tissue; Determination of expressed RNA level of inflammatory cytokines in BALF (Experimental Example 4) to confirm the synergistically potent inhibiting activity on the expressed RNA level of inflammatory cytokines in BALF; Lung histology (Experimental Example 5) to confirm the anti-asthmatic effect through histopathological analysis on broncho-alveolar tissue; Brief Clinical test (Experimental Example 7) to confirm the clinical efficacy and safety in human of the inventive extract on respiratory disease etc, it has been verified that the inventive combined extract showed more potent inhibiting effect on respiratory inflammation disease than each herb extract. Therefore, the herbal extract of the present invention can be usefully used in a pharmaceutical composition, health functional food, and health supplement food for preventing and treating respiratory inflammation disease.

Technical Solution

The technical solution to solve the problem of the background art is for the development of novel herb formulation for treating and preventing a respiratory inflammation disease.

According to one aspect, the present invention provides a pharmaceutical composition comprising a combined herb extract of *Salvia plebeia* R. Br. and red ginseng, as an active ingredient for preventing and treating a respiratory inflammation disease.

The present invention also provides a health functional food comprising a combined herb extract of *Salvia plebeia* R. Br. and red ginseng for the prevention or improvement of a respiratory inflammation disease as an active ingredient.

The term "combined herb extract" defined herein comprises the combined herb extract, i.e., combined herb extract of *Salvia plebeia* R. Br. and red ginseng with the mixed ratio based on the dried weight of each extract (w/w) ranging from 0.01-100: 100-0.01 (w/w), preferably, 0.1-50: 50-0.1 (w/w), more preferably, 0.5-20: 20-0.5 (w/w), more and more preferably, 1-10:10-1 (w/w), most preferably, 1-5:5-1 (w/w) in the present invention.

Specifically, the term "extract" defined herein comprises the extract soluble in distilled water, $C_1$-$C_4$ alcohols or the mixtures thereof, preferably, water, ethanol or the mixture thereof, more preferably, water or 10%-90% (v/v) ethanol in water, most preferably, water or 20%-80% (v/v) ethanol in water.

The term "*Salvia plebeia* R. Br" or "red ginseng" defined herein comprises the whole body, root, stem or flower of "*Salvia plebeia* R. Br" or "red ginseng" to use as a basic extraction material.

The term "red ginseng" defined herein comprises the processed ginseng of 2-10 years old, preferably, 3-8 years old; more preferably, 5-7 years old root of ginseng selected from the group consisting of *Panax ginseng, Panax quinquefolia, Panax notoginseng, Panax vietnamensis, Panax elegatior, Panax wangianus* and *Panax bipinratifidus*.

Specifically, the term "red ginseng" defined herein comprises the processed ginseng prepared by the steps comprising: drying 2-10 years old, preferably, 3-8 years old, more preferably, 5-7 years old root of ginseng selected from the group consisting of *Panax ginseng, Panax quinquefolia, Panax notoginseng, Panax vietnamensis, Panax elegatior, Panax wangianus* and *Panax bipinratifidus* at 1° C.-60° C., preferably, room temperature for 1-24 hours, preferably, 1-3 hours to prepare the $1^{st}$ dried ginseng at $1^{st}$ step; washing the dried ginseng with water and drying to remove the water at $2^{nd}$ step; steaming the dried ginseng at 60° C.-120° C., preferably, 80° C.-110° C., for 1-48 hours, preferably, 1-12 hours, more preferably, 1-3 hours to prepare the $1^{st}$ steamed ginseng at $3^{rd}$ step; drying the $1^{st}$ steamed ginseng at 30° C.-80° C., preferably, 40° C.-70° C. for 1-72 hours, preferably, 2-48 hours, more preferably, 4-12 hours to prepare the $1^{st}$ dried steamed ginseng containing 40-70% (w/w), preferably, 45-55% (w/w) water content at $4^{th}$ step; and drying the $1^{st}$ dried steamed ginseng at 10° C.-60° C., preferably, 15° C.-35° C., for 1-20 days, preferably, 6-20 days to obtain the final dried red ginseng containing 10-20% (w/w), preferably, 12-17% (w/w) water content at $5^{th}$ step.

The term "combined herb extract of "*Salvia plebeia* R. Br." and "red ginseng" defined herein can be prepared by the procedure comprising the steps; of slicing and washing the whole body, root, stem or flower of "*Salvia plebeia* R. Br" or "red ginseng" to use as a basic extraction material at $1^{st}$ step; adding 1-20 fold volume, preferably, 4-8 fold volume of extracting solvent selected from the group consisting of distilled water, $C_1$-$C_4$ alcohols or the mixtures thereof, preferably, water, ethanol or the mixture thereof to the basic extraction material at $2^{nd}$ step; extracting each solution with the extraction method by the extraction with hot water, cold water, or ultra-sonication extraction, preferably, hot water extraction at the temperature ranging from 50° C.-120° C., preferably, about 80° C.-100° C., for the period ranging from 1 to 48 hours, preferably, 2 to 24 hours at $3^{rd}$ step; repeating the above-described extraction process to collect each filtrate with filtration, drying through freeze drying, natural air drying or hot air drying process, preferably freeze drying process to obtain respective dried extract of *Salvia plebeia* R. Br. and red ginseng at $4^{th}$ step; and mixing the respective dried extract of each herb (*Salvia plebeia* R. Br. and red ginseng) with the mixed ratio based on the dried weight of each herb (w/w) ranging from 0.01-100: 100-0.01 (w/w), preferably, 0.1-50: 50-0.1 (w/w), more preferably, 0.5-20: 20-0.5 (w/w), more and more preferably, 1-10:10-1 (w/w), most preferably, 1-5:5-1 (w/w) to prepare inventive combined extract of the present invention.

Specifically, the term "respiratory inflammation disease" disclosed herein comprises all the respiratory inflammation disease, for example, not intended to limit thereto, a rhinitis, otitis media, laryngopharyngitis, tonsillitis, pneumonia, asthma, COPD (Chronic Obstructive Pulmonary Disease) and the like.

An inventive herb extract may be prepared in accordance with the following preferred embodiment.

For example, the present invention also provides a method for preparing the inventive herb extract comprising the steps of; of slicing and washing the whole body, root, stem or flower of "*Salvia plebeia* R. Br" or "red ginseng" to use as a basic extraction material at $1^{st}$ step; adding 1-20 fold volume, preferably, 4-8 fold volume of extracting solvent selected from the group consisting of distilled water, $C_1$-$C_4$ alcohols or the mixtures thereof, preferably, water, ethanol or the mixture thereof to the basic extraction material at $2^{nd}$ step; extracting each solution with the extraction method by the extraction with hot water, cold water, or ultra-sonication extraction, preferably, hot water extraction at the temperature ranging from 50° C.~120° C., preferably, about 80° C.~100° C., for the period ranging from 1 to 48 hours, preferably, 2 to 24 hours at $3^{rd}$ step; repeating the above-described extraction process to collect each filtrate with filtration, drying through freeze drying, natural air drying or hot air drying process, preferably freeze drying process to obtain respective dried extract of *Salvia plebeia* R. Br. and red ginseng at $4^{th}$ step; and mixing the respective dried extract of each herb (*Salvia plebeia* R. Br. and red ginseng) with the mixed ratio based on the dried weight of each herb (w/w) ranging from 0.01-100:100-0.01 (w/w), preferably, 0.1-50: 50-0.1 (w/w), more preferably, 0.5-20: 20-0.5 (w/w), more and more preferably, 1-10:10-1 (w/w), most preferably, 1-5:5-1 (w/w) to prepare inventive combined extract of the present invention.

It is another object of the present invention to provide a process for preparing the extract of the present invention as described above for the preparation of composition effective in treating or preventing the purposed diseases.

It is still another object of the present invention to provide a pharmaceutical composition or health functional food comprising the herb extract of the above-mentioned herb obtained by the above described process as an active ingredient for preventing and treating a respiratory inflammation disease.

The inventive composition of the present invention shows potent treating effect on respiratory inflammation disease, which is confirmed by various experiments, for example, determination of the cell number of BAL (bronchoalveolar lavage) (Experimental Example 1) to confirm synergistically potent inhibiting activity on the cell number in BAL (bronchoalveolar lavage); Determination of CD11b+/Gr-1+ ratio in leukocyte within BAL fluid (Experimental Example 2) to confirm synergistically potent inhibiting activity on the CD11b+/Gr-1+ ratio in leukocyte within BAL fluid; Determination of expressed RNA level of inflammatory cytokines in lung tissue (Experimental Example 3) to confirm the synergistically potent inhibiting activity on the expressed RNA level of inflammatory cytokines in lung tissue; Determination of expressed RNA level of inflammatory cytokines in BALF (Experimental Example 4) to confirm the synergistically potent inhibiting activity on the expressed RNA level of inflammatory cytokines in BALF; Lung histology (Experimental Example 5) to confirm the anti-asthmatic effect through histopathological analysis on broncho-alveolar tissue; Brief Clinical test (Experimental Example 7) to confirm the clinical efficacy and safety in human of the inventive extract on respiratory disease etc, it has been verified that the inventive combined extract showed more potent inhibiting effect on respiratory inflammation disease than each herb extract. Therefore, the herbal extract of the present invention can be usefully used in a pharmaceutical composition, health functional food, and health supplement food for preventing and treating respiratory inflammation disease.

The pharmaceutical composition for treating purposed diseases could contain about 0.01 to 99 w/w % the above herb extract of the present invention based on the total weight of the composition.

However, the amount and each component of the above-mentioned composition can be varied with the patient's condition, development of patient's disease, the sort of disease etc.

The inventive composition may additionally comprise conventional carrier, adjuvants or diluents in accordance with a using method.

The herb composition according to the present invention can be formulated in oral dosage form such as powder, granule, tablet, capsule, suspension, emulsion, syrup, aerosol and the like; topical preparation; or injection solution. The herb composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, magnesium stearate and mineral oil. The formulations may additionally include excipients such as fillers, bulking agents, binders, wetting agents, disintegrating agents, surfactants, diluents and the like. The solid oral dosage form comprises tablet, pill, powder, granule, capsule and the like and the solid oral dosage form is prepared by adding at least one excipient such as starch, calcium carbonate, sucrose, lactose or gelatin and the like to the herb extract. Lubricant such as magnesium stearate or talc may be used. The aqueous oral dosage form comprises suspension, oral solution, emulsion, syrup and the aqueous oral dosage form may comprise several excipients such as wetting agents, sweetener flavoring agents, preservatives, as well as water, liquid paraffin. The parenteral dosage form comprises sterilized aqueous solution, non-aqueous solvent, suspension, emulsion, lyophilized preparation, suppository, and the like. Suitable examples of the carriers include propylene glycol, polyethylene glycol, vegetable oils such as olive oil, injectable ester such as ethyl oleate. Base for suppository may include witepsol, macrogol, tween 61, cacao butter, laurin, glycerogelatine etc., but are not limited to them.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 0.01 mg/kg to 10 g/kg, preferably, 1 mg/kg to 1 g/kg by weight/day of the inventive composition of the present invention. The dose may be administered in a single or multiple doses per day.

The pharmaceutical composition of present invention can be administered to a subject animal such as mammals (rat, mouse, domestic animals or human) via various routes. All modes of administration are contemplated, for example, administration can be made orally, rectally or by intravenous injection.

It is the other object of the present invention to provide a method of treatment or prevention comprising administering of the composition comprising the combined herb extract of *Salvia plebeia* R. Br. and red ginseng, as an active ingredient to a subject in need of treatment or prevention of a respiratory inflammation disease.

It is another object of the present invention to provide a use of the combined herb extract of *Salvia plebeia* R. Br. and red ginseng as an active ingredient for manufacture of medicament employed for treating or preventing a respiratory inflammation disease in human or mammal. In accordance with one aspect of the present invention, there provided a health functional food comprising the combined herb extract of *Salvia plebeia* R. Br. and red ginseng for the prevention or improvement of a respiratory inflammation disease as an active ingredient.

The term "a health functional food" defined herein comprises the functional food having enhanced functionality such as physical functionality or physiological functionality by adding the extract of the present invention to conventional food to prevent or improve the purposed diseases in human or mammal and stipulated by the Law for Health Functional Foods 6727 in Republic of Korea.

The health functional food composition for preventing and improving purposed diseases could contain about 0.01 to 95 w/w %, preferably 1 to 80 w/w % of the above herb composition of present invention based on the total weight of the composition.

Moreover, the inventive extract of the present invention also can be used as a main component or additive and aiding agent in the preparation of various functional health food and health supplement food for the prevention or improvement of a respiratory inflammation disease.

The inventive health functional food may be prepared and processed by the form of pharmaceutically acceptable dosage form such as powder, granule, tablet, capsule, pills, suspension, emulsion, syrup and the like; or the functional health food form such as tea bag, leached tea, health beverage type and the like.

It is the other object of the present invention to provide a health supplement food comprising the combined herb extract of *Salvia plebeia* R. Br. and red ginseng, as a main component, for the prevention or improvement of a respiratory inflammation disease.

The above-mentioned term "as a main component" means that the above health supplement food comprises about 30 to 99 (w/w %), preferably 50 to 99 (w/w %), more preferably 70 to 99 (w/w %) of the inventive extract of present invention based on the total weight of the composition.

When the combined herb extract of the present invention is used as a component in the health functional beverage composition, the health functional beverage composition can comprise other component such as flavoring agent or natural carbohydrate without limits like that typical beverage composition. Examples of the natural carbohydrate comprise monosaccharide such as glucose, fructose etc; disaccharide such as maltose, sucrose etc; and polysaccharide, for example, sugar such as dextrin, cyclodextrin, and sugar alcohol such as xylitol, sorbitol, erythritol. Natural flavoring agent (thaumatin, stevia extract (rebaudioside A, glycyrrhizin, etc)) and synthetic flavoring agent (saccharin, aspartame, etc) may be added in the health functional beverage composition. The amount of natural carbohydrate generally ranges from about 1 to 20 g, preferably about 5 to 12 g per 100 ml of the present composition.

When the combined herb extract of the present invention is used as a food additive of the health food, the combined herb extract may be added intact or used with other food ingredient according to general process. Examples of the food comprises meat products, sausage, bread, chocolate, candy, snack, cracker, biscuit, pizza, ramen, noodle products, chewing gum, dairy products such as ice cream, soup, beverage, tea, drinks, alcohol drink, vitamin complex etc, but not intended herein to limit thereto, for preventing or improving of purposed disease.

The other components than aforementioned composition are various nutrients, a vitamin, a mineral or an electrolyte, synthetic flavoring agent, a coloring agent and improving agent in case of cheese, chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Also, above described extract can be added to food or beverage for prevention and improvement of purposed disorder. The amount of above described extract in food or beverage as a functional health food or health supplement food may generally range from about 0.01 to 15 w/w % of total weight of food for functional health food composition. And the extract of the present invention may be added 0.02 to 5 g, preferably 0.3 to 1 g per 100 ml in health beverage composition.

Advantageous Effects

As described in the present invention, inventive combined herb composition shows potent treating effect on respiratory inflammation disease and the combined herb composition shows more potent treating effect on a respiratory inflammation than the individual herb composition, which is confirmed by various experiments, for example, determination of the cell number of BAL (bronchoalveolar lavage) (Experimental Example 1); Determination of CD11b+/Gr-1+ ratio in leukocyte within BAL fluid (Experimental Example 2); Determination of expressed RNA level of inflammatory cytokines in lung tissue (Experimental Example 3); Determination of expressed RNA level of inflammatory cytokines in BALF (Experimental Example 4); Lung histology (Experimental Example 5); Brief Clinical test (Experimental Example 7) etc, it has been verified that the inventive combined extract showed more potent inhibiting effect on respiratory inflammation disease than each herb extract. Therefore, the herbal extract of the present invention can be usefully used in a pharmaceutical composition, health functional food, and health supplement food for preventing and treating respiratory inflammation disease.

DESCRIPTION OF DRAWINGS

FIG. 1 shows the histopathological analysis on bronchoalveolar tissue stained by staining agent (NC: Normal Control group; AIG: Asthma induced Group; CB3: test sample group treated with CB3 combined extract).

BEST MODE

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Examples and Experimental Examples are intended to further illustrate the present invention without limiting its scope.

Comparative Example 1

Preparation of Extract of *Salvia plebeia* R. Br.

1.5 kg of dried *Salvia plebeia* R. Br. (distributed on Buan-gun, Jeollabuk-do, Republic of Korea) was added to 22.5 L of 30% ethanol to perform extraction with reflux extraction for 4 hors at 80° C.±2° C. twice. The residue was filtered with filter paper to afford extract and the filtrated extract was concentrated under 650±30 mmHg at 52.5° C.±2.5° C. The concentrated extract was sterilized for 1 hour at 85.0° C.±2.0° C. and cooled to 55° C. The sterilized extract was dried with freeze dryer (KL-8, SeoGang Engineering Co. Ltd., inlet temp.: 190° C.±10° C., outlet temp.: 95° C.±5° C.) to afford 458 g of dried 30% ethanol extract of *Salvia plebeia* R. Br. (designated as "SP" hereinafter), which is used as a comparative test sample 1 in following experiment.

Comparative Example 2

Preparation of Red Ginseng Extract
2-1. Preparation of Red Ginseng
10 kg of dried 6 years-old fresh ginseng root (*Panax ginseng* C. A. Meyer) procured from KT&G Corp (100, Pyeongchon-dong, Seo-gu, Daejeon, Republic of Korea, cultivated from geumsangun chungcheongnamdo, South Korea) was washed with distilled water and further washed again for 30 mins using by conventional ultrasonic cleaner (Branson 5210, Emerson Electric Co. United States). The washed fresh ginseng was subjected to steaming process with vapor at about 80° C.-100° C. for 90-110 mins using by steaming apparatus (KMC-1221, Jeiotech Co. Ltd., Daejeon, Korea) and dried at about 60° C.-65° C. for 9 hours using by drying apparatus (KMC-1202D3, Jeiotech Co. Ltd., Daejeon, Korea) to afford the $1^{st}$ dried ginseng (water content: 45-55%). The $1^{st}$ dried ginseng was subjected to $2^{nd}$ drying process in drying room for 13-17 days to make red ginseng (water content: about 14%, designated as "RG1" hereinafter).

2-2. Preparation of Red Ginseng Extract 500 g of red ginseng prepared from the above step was subjected to $3^{rd}$ drying process at about 100° C.-120° C. for 15-20 mins using by far-infrared drying apparatus (Korea Energy Technicals Co. Ltd., HKD-LAB) and cut into pieces. The dried red ginseng was poured into 4-8 folds distilled water and perform reflux extraction for 8-12 hours at 85° C. The solution was filtered with filter paper and cooled to 0° C.-10° C. The residue was poured into 4-8 folds distilled water and perform reflux extraction for 8-12 hours at 85° C. and the extraction was repeated 4 times. The extract was collected, filtered with filter paper and cooled to 0° C.-10° C. The cooled extract was centrifuged for 10-20 mins, at 4° C. at the speed of 5,000-8,000 rpm to remove unnecessary debris using by centrifuge apparatus (Supra22K, Hanil Science Medicals Co. Ltd., Daejeon City) and evaporated with evaporator at 50° C.-60° C. to remove water to obtain the concentrated extract (71° brix), Finally, the concentrated red ginseng extract was dissolved in distilled water to make diluted extract (15° brix) and performed spray drying to afford 230 g of a red ginseng extract (designated as "RG" hereinafter), which was used as a comparative sample 2 in following experiments.

Example 1

Preparation of Combined Formulation (CB1-CB7)

The dried extract of *Salvia plebeia* R. Br. and red ginseng extract prepared in the above Comparative Example was thoroughly mixed with different mixed weigh ratios (See Table 1) using by mixer (Vortex genie-2, scientific industries, USA) to obtain the various kinds of invention formulation (designated as "CB1-CB7" hereinafter), which are used as a test samples in following experiment.

TABLE 1 various kinds of invention formulation

| Example | *weight ratio of A:B | combination name |
|---|---|---|
| Example 1-1 | 0.3:1 | CB1 |
| Example 1-2 | 1:1 | CB2 |
| Example 1-3 | 2:1 | CB3 |
| Example 1-4 | 3:1 | CB4 |
| Example 1-5 | 4:1 | CB5 |
| Example 1-6 | 5:1 | CB6 |
| Example 1-7 | 10:1 | CB7 |

*A: extract of *Salvia plebeia* R. Br./B: red ginseng extract

Experimental Example 1

Determination of the Cell Number of BAL (Bronchoalveolar Lavage).

In order to confirm synergistically potent inhibiting activity on the cell number in BAL (bronchoalveolar lavage) of the inventive combinations than the comparative Examples, following test was performed by the method disclosed in the literature (Schins et al., *Toxicol. Appl. Pharmacol.*, 195(1), pp 1-11, 2004; Smith et al., *Toxicol. Sci.*, 93(2), pp 390-399, 2006).

1-1. Test Procedure

Specific pathogen-free female BALB/c mice (about 20 g), aged 6 weeks, which were routinely screened serologically for relevant respiratory pathogens, were purchased from ORIENT Co. (Seoul, Korea) and acclimated with the experimental environment for 1 week. The mice were sensitized by INT (Intra-Nazal-Trachea) injection of 50 μL of fine dust mixture prepared by mixing alum with fine dust mixture (025 mg/ml of coal, 10 mg/ml of fly ash and 0.25 mg/ml of diesel exhaust particle) to be final concentration of 8%, at 3rd day and $6^{th}$ day after the initial sensitization to prepare asthma-induced animal model.

Briefly, mice were divided into four groups of which each group consists of 6 mice, i.e., (a) normal control group (NC): the groups not-treated with fine dust mixture; (b) asthma-induced group (AIG): the groups treated with fine dust mixture to induce asthma; (c) comparative groups: the groups orally treated with comparative groups prepared in Comparative Examples by dissolving in 0.5% CMC (sodium carboxymethyl cellulose, 419273, Sigma-Aldrich) every day for 10 days; and (d) test sample groups orally treated with test sample groups prepared in Examples by dissolving in 0.5% CMC (sodium carboxymethyl cellulose, 419273, Sigma-Aldrich) every day for 10 days.

At $11^{th}$ day after the experiment, the mice were performed to autopsy and the BAL (bronchoalveolar lavage) fluid of mice was collected.

1-2. Test Result

As shown in Table 2, the total cell number in BAL (bronchoalveolar lavage) fluid in test sample group treated with inventive combinations was synergistically reduced than those in the comparative groups treated with the sole extract of *Salvia plebeia* R. Br. (SP) or red ginseng extract (RG), respectively.

TABLE 2

The total cell number in BAL fluid

| | total Cell number ($\times 10^5$ cells/ml) | Inhibition percentage (%)* |
|---|---|---|
| NC | 32.3 ± 6.14 | |
| AIG | 117.0 ± 8.5 | |
| SP | 65.0 ± 5.24 | 44% |
| RG | 67.3 ± 5.74 | 42% |
| CB1 | 47.5 ± 5.36 | 59% |
| CB2 | 40.1 ± 11.63 | 66% |
| CB3 | 37.8 ± 2.13 | 68% |
| CB4 | 33.3 ± 1.75 | 72% |
| CB5 | 44.1 ± 3.28 | 62% |
| CB6 | 49.7 ± 8.30 | 58% |
| CB7 | 54.8 ± 7.26 | 53% |

*data based on the inhibition of AIG

Experimental Example 2

Determination of CD11b+/Gr-1+ Ratio in Leukocyte within BAL Fluid.

In order to confirm synergistically potent inhibiting activity on the CD11b+/Gr-1+ ratio in leukocyte within BAL fluid of the inventive combinations than the comparative Examples, following test was performed by the method disclosed in the literature (Beutner E. H., *bacteriological Reviews*, 25(1), pp 49-76, 1961).

2-1. Test Procedure

BAL (bronchoalveolar lavage) fluid of mice collected from Experimental Example 1 was performed to specific fluorescent antibody staining method using by fluorescence-labeled CD11b antibody (553310, BD Biosciences, San Jose, Calif., USA) and Gr-1 antibody (553128, BD Biosciences, San Jose, Calif., USA). The CD11b+/Gr-1+ ratio in total leukocyte within BAL fluid was determined according to FACS method (Fluorescence-activated cell sorting, BD Biosciences, San Jose, Calif., USA).

2-2. Test Result

As shown in Table 3, the CD11b+/Gr-1+ ratio in total leukocyte within BAL fluid in test sample group treated with inventive combinations was synergistically reduced than those in the comparative groups treated with the sole extract of *Salvia plebeia* R. Br. (SP) or red ginseng extract (RG), respectively.

TABLE 3

The CD11b+/Gr-1+ ratio in total leukocyte within BAL fluid

| | CD11b+/Gr-1+ ratio (%) | Inhibition percentage (%)* |
|---|---|---|
| NC | 7.1 ± 0.2 | |
| AIG | 51.2 ± 3.6 | |
| SP | 35.3 ± 3.2 | 36% |
| RG | 40.8 ± 1.6 | 20% |
| CB1 | 29.7 ± 1.5 | 42% |
| CB2 | 25.1 ± 4.6 | 51% |
| CB3 | 21.3 ± 2.7 | 58% |
| CB4 | 19.1 ± 3.6 | 63% |
| CB5 | 24.9 ± 1.6 | 51% |
| CB6 | 28.4 ± 2.5 | 44% |
| CB7 | 32.0 ± 3.6 | 35% |

*data based on the inhibition of AIG

Experimental Example 3

Determination of Expressed RNA Level of Inflammatory Cytokines in Lung Tissue

In order to confirm the synergistically potent inhibiting activity on the expressed RNA level of inflammatory cytokines in lung tissue of the inventive combinations than the comparative Examples, following RT-PCR (Realtime quantitative polymerase chain reaction) test was performed by the method disclosed in the literature (Adelroth E., *Cancer Respir J.*, pp 18A-21A, 1998).

3-1. Test Procedure (1) Isolation and Extraction of RNA from Lung Tissue

The lung tissue was delivered rather than BAL (bronchoalveolar lavage) fluid of mice according to the method disclosed in Experimental Example 1. The delivered lung tissue was added to 500 mL of RNAzolB (Tel-Test, Friendswood, USA) and mashed to be dissolved. 50 mL of $CHCl_3$ was added to the suspension and stirred again for 15 seconds. the suspension was left alone in ice for 15 mins and centrifuged at the speed of 13,000 rpm. About 200 mL of collected supernatant was added to the equivalent amount of 2-propanol (19516, Sigma-Alrich, USA) and stirred gently to be left alone in ice for 15 mins. The solution was centrifuged again at the speed of 13,000 rpm, washed with 80% ethanol and dried in vaccuo for 3 mins to extract RNA. The extracted RNA was dissolved in 20 mL of distilled water treated with DEPC (Diethyl pyrocarbonate, 750023, Thermo Scientific, Massachusetts, USA), and inactivated at 75° C. to be used in cDNA (first strand complementary DNA).

(2) cDNA Synthesis

2 μg of total RNA was added to 2 U/tube DNase I (AB0620, Thermo Scientific, Massachusetts, USA), reacted for 30 mins at 35° C., denatured for 10 mins and added to the reaction mixture consisting of 2.5 mL of 10 mM dNPTs mix (4030, TaKaRa Shiga, Japan), 1 mL of random sequence hexanucleotides (N8080127, Thermo Scientific, Massachusetts, USA), 1 mL of RNase inhibitor (2313A, TaKaRa Shiga, Japan), 1 mL of 100 mM DTT (4029, TaKaRa Shiga, Japan) and 4.5 mL of 5×RT buffer (M5313, Promega, Wisconsin-Madison, USA). The solution was added to 4.5 mL of M-MLV RT (M1701, Promega, Wisconsin-Madison, USA) and dissolved in distilled water treated with DEPC (Diethyl pyrocarbonate, 750023, Thermo Scientific, Massachusetts, USA) to be final volume of 20 mL. After thoroughly stirring, the solution was centrifuged for 5 seconds at the speed of 2000 rpm, reacted in heating block (Multi-block heater, TRIPUNITHURA, USA) at 37° C. for 60 mins to synthesize cDNA and then left alone for 5 mins at 95° C. to inactivate M-MLV RT. The synthesized cDNA was used in PCR method.

(3) PCR

The synthesized cDNA was performed to RT-PCR method according to the procedure disclosed in the literature (Galli et al., *Nat. Immunol.*, 6(2), pp 135-142, 2005).

Sper-Taqman PCR Master mix (4304437, Applied Biosystems, San Mateo, USA) as well as various primers disclosed in Table 4 (final concentration: 200 nM) were used in the RT-PCR method. RT-PCR was performed by pre-denaturing 2 mins at 50° C., for 10 mins at 94° C., and reacting for 40 cycles, i.e., 0.15 mins at 95° C. and for 1 min at 60° C. GAPDH (Glyceraldehyde-3-phosphatedehydrogenase, 4352339E, Thermo Scientific, Massachusetts, USA) was used as an internal standard.

TABLE 4

The used primers in RT-PCR method

| Target-gene | primer | sequences | Sequence I. D. |
|---|---|---|---|
| MUC5AC | Forward | 5'-AGAATATCTTTCAGGACCC CTGCT-3' | 1 |
| | Reverse | 5'-ACACCAGTGCTGAGCATAC TTTT-3' | 2 |
| CCR5 | Forward | 5'-ATTCTCCACACCCTGTTTC G-3' | 3 |
| | Reverse | 5'-AAGGTGGTCAGGAGGAGGA C-3' | 4 |
| DAPDH-VIC | Probe | 5'-CATGTTCCAGTATGACTCC ACTCACG-3 | 5 |

3-2. Test Result

As shown in Table 5, the expressed RNA level of inflammatory cytokines in lung tissue such as MUC5AC, CCR5 etc in test sample group treated with inventive combinations was synergistically reduced than those in the comparative groups treated with the sole extract of *Salvia plebeia* R. Br. (SP) or red ginseng extract (RG), respectively.

TABLE 5

The expressed RNA level of inflammatory cytokines in lung tissue

|  | MUC5AC | | CCR5 | |
| --- | --- | --- | --- | --- |
|  | expressed level | Inhibition percentage (%)* | expressed level | Inhibition percentage (%)* |
| NC | 1.66 ± 0.94 |  | 0.76 ± 0.19 |  |
| AIG | 5.29 ± 0.75 |  | 8.80 ± 1.59 |  |
| SP | 2.92 ± 0.84 | 45% | 4.99 ± 1.95 | 43% |
| RG | 3.40 ± 0.63 | 36% | 7.93 ± 1.65 | 10% |
| CB1 | 2.62 ± 0.31 | 50% | 4.69 ± 0.69 | 47% |
| CB2 | 2.46 ± 1.20 | 53% | 4.20 ± 0.71 | 52% |
| CB3 | 2.22 ± 0.98 | 58% | 4.14 ± 1.39 | 53% |
| CB4 | 1.81 ± 0.72 | 66% | 3.36 ± 0.90 | 62% |
| CB5 | 2.12 ± 0.63 | 60% | 3.98 ± 0.87 | 55% |
| CB6 | 2.38 ± 0.28 | 55% | 4.03 ± 1.64 | 54% |
| CB7 | 2.65 ± 0.83 | 50% | 4.90 ± 0.76 | 44% |

*data based on the inhibition of AIG

Experimental Example 4

Determination of Expressed RNA Level of Inflammatory Cytokines in BALF

In order to confirm the synergistically potent inhibiting activity on the expressed RNA level of inflammatory cytokines in BALF of the inventive combinations than the comparative Examples, following ELISA (Enzyme-Linked Immuno Sorbent Assay) test was performed by the method disclosed in the literature (Brandt E. B. et al., *J. Allergy Clin. Immunol.*, 132(5), pp 1194-1204, 2013).

4-1. Test Procedure

BAL (bronchoalveolar lavage) fluid of mice collected from Experimental Example 1 was performed to ELISA (Enzyme-Linked Immuno Sorbent Assay) test to determine the level of IL-17A, TNF-alpha, MIP2, and CXCL-1, similarly to the method disclosed in Experimental Example 3. IL-17A antibody (M1700, R&D Systems, Minneapolis, USA), TNF-alpha antibody (MTA00B, R&D Systems, Minneapolis, USA), MIP2 antibody (MM200, R&D Systems, Minneapolis, USA), and CXCL-1 antibody (MKC00B, R&D Systems, Minneapolis, USA) were diluted with buffer solution and coated with micro cell to incubate at 95° C., for 16 hours. Each well was washed with washing buffer solution three times and 100 μL of 10 fold diluted serum was inoculated thereto. After being left alone at room temperature for 1 hour, the well was washed twice and 100 μL of Avidin-HRP-conjugated antibody (DY007, R&D System, Minneapolis, USA) was treated therewith to be left alone at room temperature for 1 hour. After washing again, 100 μL of TMB substrate (DY999, R&D System, Minneapolis, USA) was inoculated thereto to be left alone in shadow for 30 mins. 50 μL of stop solution (DY994, R&D System, Minneapolis, USA) was treated therewith and then the absorbance of the solution was determined at 450 nm.

4-2. Test Result

As shown in Table 6, the expressed RNA level of inflammatory cytokines in BALF such as IL-17A, TNF-alpha, MIP2, and CXCL-1 etc in test sample group treated with inventive combinations was synergistically reduced than those in the comparative groups treated with the sole extract of *Salvia plebeia* R. Br. (SP) or red ginseng extract (RG), respectively.

Accordingly, it has been confirmed that the inventive combinations showed more potent reducing effect on the expressed RNA level of inflammatory cytokines in BALF such as IL-17A, TNF-alpha, MIP2, and CXCL-1 etc than those in the comparative groups treated with the sole extract of *Salvia plebeia* R. Br. (SP) or red ginseng extract (RG), respectively and therefore, they are useful in treating or preventing the asthma disease, an allergic disease or COPD in airway.

TABLE 6

The expressed RNA level of inflammatory cytokines in BALF

| | level (pg/mL)/inhibition percentage (%)* | | | |
| --- | --- | --- | --- | --- |
| | IL-17A | TNF-alpha | MIP2 | CXCL-1 |
| NC | 4.4 | 45.6 | 70.7 | 95.8 |
| AIG | 13.2 | 87.2 | 164.5 | 231.1 |
| SP | 7.9/40% | 47.2/46% | 97.1/41% | 152.5/34% |
| RG | 9.6/27% | 53.2/39% | 104.4/37% | 162.9/30% |
| CB1 | 7.8/41% | 29.5/66% | 77.8/53% | 139.8/40% |
| CB2 | 7.8/41% | 30.0/66% | 75.0/54% | 138.6/40% |
| CB3 | 7.5/43% | 28.1/68% | 72.9/56% | 137.5/41% |
| CB4 | 6.0/55% | 20.3/77% | 64.1/61% | 130.1/44% |
| CB5 | 7.1/46% | 36.3/58% | 79.1/52% | 145.6/37% |
| CB6 | 7.2/45% | 46.6/47% | 84.3/49% | 150.9/35% |
| CB7 | 7.8/41% | 46.0/47% | 89.5/46% | 150.4/35% |

*data based on the inhibition of AIG

Experimental Example 5

Lung Histology

In order to confirm the anti-asthmatic effect of test samples prepared in Examples, following histopathological analysis on broncho-alveolar tissue was performed using by H&E staining and M-T staining method according to the method disclosed in the literature (Nandedkar S D. et al., *Blood*, 111(6), pp 2529-2538, 2008).

5-1. Test Procedure

The lung tissue was delivered rather than BAL (broncho-alveolar lavage) fluid of mice according to the method disclosed in Experimental Example 1. The delivered lung tissue was fixed for 24 h in 10% neutral-buffered formalin solution (F8775, Sigma-Aldrich, USA), dissected and washed with running water for 8 hours. After being embedded in epoxy (A3183, Sigma-Aldrich, USA), the tissue was made into 4-μm thickness sections with microtome (leica RM2265, Wetzlar, Germany) and the section was stained with Masson-Trichrome (HT10516, Sigma-Aldrich, USA) to observe histopathological analysis on broncho-alveolar tissue using by optical microscope (Bright Microscope, Tokyo, Japan).

5-2. Test Result

As shown in FIG. 1 showing the histopathological analysis on broncho-alveolar tissue, the increase of collagen fiber as well as the hypertrophy of tracheal muscle were also found in the asthma-induced group comparing with normal group and the significant decrease of collagen fiber and the thinning of tracheal muscle were found in test sample groups treated with inventive combination.

Experimental Example 6

Acute Toxicity Test of Oral Administration in Rat

The acute toxicity test was performed by administrating inventive extract (CB3) to 6-weeks aged SPF Sprague-Dawley rats.

250 mg/kg, 500 mg/kg, 1000 mg/kg, 5000 mg/kg of inventive extract was orally administrated to each group consisting of 2 rats and the symptoms of rats were observed for 14 days. After administrating the extract or compounds, all the clinical changes i.e., mortality, clinical signs, body weight changes was observed and blood test such as hematological test and hematological biochemistry test was performed. The abnormal changes of abdominal organ and thoracic organ were observed after autopsy.

There did not show any changes in mortality, clinical signs, body weight changes and gross findings in any group or either gender. Furthermore, there showed any toxicity in test group treated with 5000 mg/kg of inventive extract.

Accordingly, it has been confirmed that the inventive extract prepared in the present invention was potent and safe substance showing $LD_{50}$ (more than 5000 mg/kg) in oral administration.

Experimental Example 7

Brief Clinical Test.

In order to confirm the clinical efficacy and safety of the inventive extract on respiratory disease, following brief clinical test was performed.

7-1. Selection of Volunteers 30 volunteers (aged 19-70 years old) having suffered with consistent respiratory disease such as cough, sputum, dyspnea etc for more than 1 month were divided into three groups, i.e., (a) low-dosage test group consisting of 10 volunteers (orally taking 2 capsules containing 250 mg of CB3 extract/capsule, 30 mins after morning meal and evening meal, twice a day for 12 weeks); (b) high-dosage test group consisting of 10 volunteers (orally taking 2 capsules containing 500 mg of CB3 extract/capsule, 30 mins after morning meal and evening meal, twice a day for 12 weeks); and (c) placebo group consisting of 10 volunteers (orally taking 2 capsules containing 0 mg/capsule, 30 mins after morning meal and evening meal, twice a day).

7-2. Test Procedure

The brief clinical test was performed by randomized, double-blind, parallel, placebo-controlled manner in Clinical Trial Center for Functional Foods of Chon buk National University Hospital (division of Pulmonology, M. D., PARK, S. J.) and the volunteers had visited three times, i.e., (a) at $1^{st}$ day (the volunteers were randomly divided into three groups to provide three kinds of test capsules); (b) at $43^{rd}$ day (the volunteers were invited to perform pre-determined efficacy tests and to provide additional test capsules); and (c) at $85^{th}$ day (the volunteers were invited to perform pre-determined efficacy tests and to end the brief clinical test).

The pre-determined efficacy tests in the experiment consist of (1) $1^{st}$ efficacy evaluation using by SGRQ (Saint George's respiratory questionnaire) and CAT (COPD assessment test) to compare the efficacy in the test sample groups with placebo group) and (2) $2^{nd}$ efficacy evaluation were using by pulmonary function test, infection frequency, infection period, syndrome etc.

7-3. Test Result

As shown in Table 7 and Table 8, the test sample groups taking high- and low-dosage test groups showed significant treating activity comparing with placebo group.

Accordingly, it has been confirmed that the inventive combinations showed potent treating activity of respiratory disease such as COPD, asthma etc in brief clinical test and therefore, they are useful in treating or preventing the asthma disease, an allergic disease or COPD in airway.

TABLE 7

The $1^{st}$ evaluation test result

| | Analysis | | significant contents between each group (P-value)* | | | |
|---|---|---|---|---|---|---|
| | | | P vs L | | P vs H | |
| 1 | CAT score | | — | | — | |
| 2 | SGRQ score | | — | | — | |
| 3 | CAT 10< | CAT score | — | | — | |
| | | SGRQ score | — | | — | |
| 4 | CAT 10> | CAT score | — | | — | |
| | | SGRQ score | Impact 0.010 | 6 weeks | — | |
| | | | 0.041 | 12 weeks | — | |
| | | total | 0.040 | 12 weeks | — | |

P: placebo group, L; Low-dosage test group, H: high-dosage test group

TABLE 8

The $2^{nd}$ evaluation test result

| Analysis** | | | P vs L*** | | | P vs H | | |
|---|---|---|---|---|---|---|---|---|
| 1 PFT | PF | FVC (L) | <.001 | 12 Ws | | FVC (%) | 0.021 | 6 Ws |
| | | FVC (%) | 0.002 | 12 Ws | | | 0.013 | 12 Ws |
| | | | | | | FVC1 (%) | 0.047 | 6 Ws |
| | BR | FVC (L) | 0.026 | 12 Ws | | | | |
| | | FVC (%) | 0.017 | 12 Ws | | | | |
| 2 CAT 10< | PF | FVC (L) | 0.012 | 12 Ws | | FVC (L) | 0.021 | 12 Ws |
| | | FVC (%) | 0.009 | 12 Ws | | FVC (%) | 0.018 | 12 Ws |
| | | FVC1 (L) | 0.034 | 12 Ws | | | | |
| | | FVC1 (%) | 0.039 | 12 Ws | | | | |
| | BR | FVC (L) | 0.015 | 12 Ws | | — | | |
| | | FVC (%) | 0.013 | 12 Ws | | | | |
| 3 CAT 10> | PF | FVC (L) | 0.033 | 12 Ws | | — | | |
| | BR | | | | | | | |
| 4 cytokine | | | — | | | — | | |
| 5 hs-CRP, ESR, CBC | | | — | | | — | | |
| 6 mRNA | | | — | | | — | | |
| 7 IF, IP, SY | | NC | PD | 0.045 | | NC | PD | 0.014 |
| | | Cough | PD | 0.046 | | Cough | PD | 0.027 |

*P: placebo group, L; Low-dosage test group, H: high-dosage test group
**PFT: Pulmonary Function Test, PF: Pulmonary Function, BR: Bronchodilator response, hs-CRP: High sensitive C-reactive protein, ESR: Erythrocyte sedimentation rate, CBC: Complete blood count, IF: infection frequency, IP: infection period, SY: syndrome
**FVC (L): Forced vital capacity (liter), FVC (%): Forced vital capacity, Ws: weeks, NC: nasal Congestion, PD: Period

MODE FOR INVENTION

Hereinafter, the formulating methods and kinds of excipients will be described, but the present invention is not limited to them. The representative preparation examples were described as follows.

Preparation of Injection
CB1 extract: 100 mg
Sodium metabisulfite: 3.0 mg
Methyl paraben: 0.8 mg
Propyl paraben: 0.1 mg Distilled water for injection: optimum amount Injection preparation was prepared by dissolving active component, controlling pH to about 7.5 and then filling all the components in 2 ml ample and sterilizing by conventional injection preparation method.

Preparation of Powder
  CB2 extract: 500 mg
  Corn Starch: 100 mg
  Lactose: 100 mg
  Talc: 10 mg Powder preparation was prepared by mixing above components and filling sealed package.

Preparation of Tablet
  CB3 extract 200 mg
  Corn Starch 100 mg
  Lactose 100 mg
  Magnesium stearate optimum amount Tablet preparation was prepared by mixing above components and entabletting.

Preparation of Capsule
  CB4 extract: 100 mg
  Lactose: 50 mg
  Corn starch: 50 mg
  Talc: 2 mg
  Magnesium stearate optimum amount Tablet preparation was prepared by mixing above components and filling gelatin capsule by conventional gelatin preparation method.

Preparation of Liquid
  CB5 extract: 1000 mg
  Sugar: 20 g
  Polysaccharide: 20 g
  Lemon flavor: 20 g Liquid preparation was prepared by dissolving active component, and then filling all the components in 1000 ml ample and sterilizing by conventional liquid preparation method.

Preparation of Health Food
  CB6 extract: 1000 mg
  Vitamin mixture: optimum amount
  Vitamin A acetate: 70 g
  Vitamin E: 1.0 mg
  Vitamin $B_{10}$: 13 mg
  Vitamin $B_2$: 0.15 mg
  Vitamin B6: 0.5 mg
  Vitamin B1: 20.2 g
  Vitamin C: 10 mg
  Biotin: 10 g
  Amide nicotinic acid: 1.7 mg
  Folic acid: 50 g
  Calcium pantothenic acid: 0.5 mg
  Mineral mixture: optimum amount
  Ferrous sulfate: 1.75 mg
  Zinc oxide: 0.82 mg
  Magnesium carbonate: 25.3 mg
  Monopotassium phosphate: 15 mg
  Dicalcium phosphate: 55 mg
  Potassium citrate: 90 mg
  Calcium carbonate: 100 mg
  Magnesium chloride: 24.8 mg The above mentioned vitamin and mineral mixture may be varied in many ways. Such variations are not to be regarded as a departure from the spirit and scope of the present invention.

Preparation of Health Beverage
  CB1 extract: 1000 mg
  Citric acid: 1000 mg
  Oligosaccharide: 100 g
  Apricot concentration: 2 g
  Taurine: g
  Distilled water: 900 ml Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the present invention provides a combined herb extract of *Salvia plebeia* R. Br. and red ginseng, as an active ingredient for preventing and treating a respiratory inflammation disease and the combined herb composition shows more potent treating effect on a respiratory inflammation than the individual herb composition, which is confirmed by various experiments, for example, determination of the cell number of BAL (bronchoalveolar lavage) (Experimental Example 1); Determination of CD11b+/Gr-1+ ratio in leukocyte within BAL fluid (Experimental Example 2); Determination of expressed RNA level of inflammatory cytokines in lung tissue (Experimental Example 3); Determination of expressed RNA level of inflammatory cytokines in BALF (Experimental Example 4); Lung histology (Experimental Example 5); Brief Clinical test (Experimental Example 7) etc, it has been verified that the inventive combined extract showed more potent inhibiting effect on respiratory inflammation disease than each herb extract. Therefore, the herbal extract of the present invention can be usefully used in a pharmaceutical composition, health functional food, and health supplement food for preventing and treating respiratory inflammation disease.

The invention claimed is:

1. A method of treating a respiratory disease, comprising administering to the subject in need thereof a composition comprising a combined herb extract of *Salvia plebeia* R. Br. and red ginseng,
   wherein a ratio based on the dried weight of extract of *Salvia plebeia* R. Br. and extract of red ginseng is 2:1 (w/w),
   wherein the combined extract is soluble in distilled water, alcohol, methanol, ethanol, butanol, or a mixed solvent thereof, and
   wherein the subject is administered a dose of 1000 to 2000 mg/day of the combined extract.

2. The method of claim 1, wherein the subject is administered a dose of 500 to 1000 mg of combined extract per dose twice a day.

3. The method of claim 2, wherein the dose is administered 30 minutes after a morning meal and 30 minutes after an evening meal.

4. The method of claim 1, wherein the subject is in need of increasing a bronchodilator response and wherein administering said composition increases the bronchodilator response in said subject.

5. The method of claim 1, wherein the subject is in need of increasing a forced vital capacity and wherein administering said composition increases the forced vital capacity in said subject.

6. The method of claim 1, wherein the subject is in need of reducing one or more symptoms selected from the group consisting of reduced bronchodilator response, reduced forced vital capacity, cough and nasal congestion, and wherein administering said composition to the subject reduces said symptoms.

7. The method of claim 1, wherein the subject has suffered from one or more symptoms selected from the group consisting of cough, sputum and dyspnea for at least a month.

8. The method of claim 1, wherein the respiratory disease is a respiratory inflammation disease.

9. The method of claim 8, wherein the respiratory inflammation disease is selected from the group consisting of rhinitis, otitis media, laryngopharyngitis, tonsillitis, pneumonia, asthma, and COPD (Chronic Obstructive Pulmonary Disease).

* * * * *